United States Patent [19]

Wade et al.

[11] 4,110,449
[45] Aug. 29, 1978

[54] 2-SUBSTITUTED BENZISOTHIAZOL-3-ONES

[75] Inventors: Peter C. Wade, Pennington, N.J.; B. Richard Vogt, Yardley, Pa.

[73] Assignee: E. R. Squibb & Sons, Inc., Princeton, N.J.

[21] Appl. No.: 799,871

[22] Filed: May 23, 1977

[51] Int. Cl.$^2$ ............... A61K 31/495; C07D 417/06
[52] U.S. Cl. ..................... 424/250; 260/293.57; 260/294.8 C; 424/263; 424/267; 544/368
[58] Field of Search ..... 260/268 BC, 301 R, 294.8 C, 260/293.57; 424/250, 263, 267

[56] References Cited

U.S. PATENT DOCUMENTS

| | | | |
|---|---|---|---|
| 2,751,392 | 6/1956 | Grogan et al. | 260/301 |
| 3,457,272 | 7/1969 | Crook et al. | 260/301 |

*Primary Examiner*—Paul M. Coughlan, Jr.
*Attorney, Agent, or Firm*—Lawrence S. Levinson; Merle J. Smith; Burton Rodney

[57] ABSTRACT

2-Substituted benzisothiazol-3-ones are provided having the structure

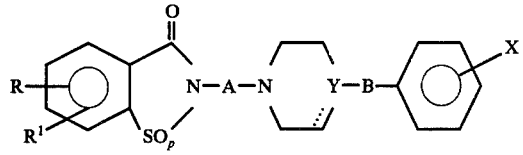

wherein R is hydrogen, halogen, lower alkyl, lower alkoxy, or nitro; $R^1$ is hydrogen, lower alkoxy or halogen, with the proviso that $R^1$ can be lower alkoxy or halogen only when R is lower alkoxy or halogen, respectively; X is hydrogen, halogen, lower alkyl, lower alkoxy, or trifluoromethyl; Y is C or N, where Y is C, represents a single or double bond, and when Y is N, represents a single bond, $p$ is 0 or 2, A is an alkylene group containing 2 to 5 carbons in the normal chain; and B is a single bond or an alkylene group containing from 1 to 3 carbons in the normal chain, and physiologically acceptable acid-addition salts thereof. These compounds have antiinflammatory activity, sedative and muscle relaxant activity. Pharmaceutical compositions containing such compounds and methods for using such compounds are also provided.

23 Claims, No Drawings

2-SUBSTITUTED BENZISOTHIAZOL-3-ONES

FIELD OF THE INVENTION

The present invention relates to 2-substituted benzisothiazol-3-ones which are useful as antiinflammatory agents, sedatives, muscle relaxants and have neuroleptic activity, and to pharmaceutical compositions containing the same, and to methods for using the same.

DISCUSSION OF PRIOR ART

Pyrazolyl- and pyrazolinyl-1,2-benzisothiazole, 1,1-dioxides such as 3-(3-methylpyrazol-1-yl)-1,2-benzisothiazole, 1,1-dioxide and 3-(4-acetyl-3-methylpyrazol-1-yl)-1,2-benzisothiazole, 1,1-dioxide, are disclosed as hypotensive agents; see Traverso et al, "Hypotensive 1,2-benzisothiazole 1,1-dioxides, I. Pyrazole and Pyrazoline Derivatives," J. Med. Chem., Sept. 1967, Vol. 10, pp 840-844.

U.S. Pat. No. 2,751,392 to Grogan et al discloses tertiary amine derivatives of N- and O-saccharin which are said to have been found suitable for the symptomatic relief of certain types of neuralgia, rheumatoid and arthritic disorders and to possess varying degrees of antihistaminic activity. The Grogen et al compounds are of the following three types:

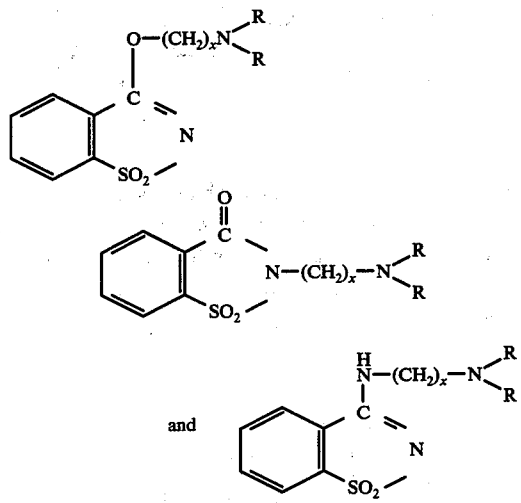

wherein $x$ is 2 to 6, R is alkyl of 1 to 6 carbons or the grouping

may represent pyrrolidine, morpholine and piperidine.

DESCRIPTION OF THE INVENTION

The 2-substituted benzisothiazol-3-ones of the invention have the following structure:

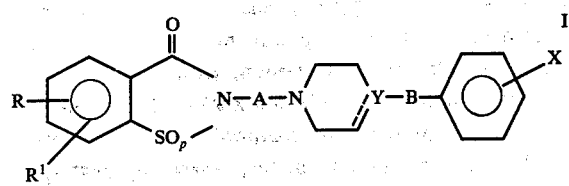

wherein R is hydrogen, halogen, lower alkyl, lower alkoxy, or nitro and $R^1$ is hydrogen, lower alkoxy or halogen, $R^1$ can be lower alkoxy or halogen only when R is lower alkoxy or halogen, respectively, R and $R^1$ in such case preferably occupying the 5- or 6-positions, respectively; X is hydrogen, halogen, lower alkyl, lower alkoxy, or trifluoromethyl; Y is C or N, where Y is N, ==== in the above formula represents a single bond, where Y is C, ==== may represent a single or double bond; p is 0 or 2, A is an alkylene group $(CH_2)_n$ containing from 2 to 5 carbons in the normal chain; and B represents a single bond or alkylene group $(CH_2)_m$ containing from 1 to 3 carbons in the normal chain.

Thus, the compounds of formula I of the invention may include compounds of the following structures:

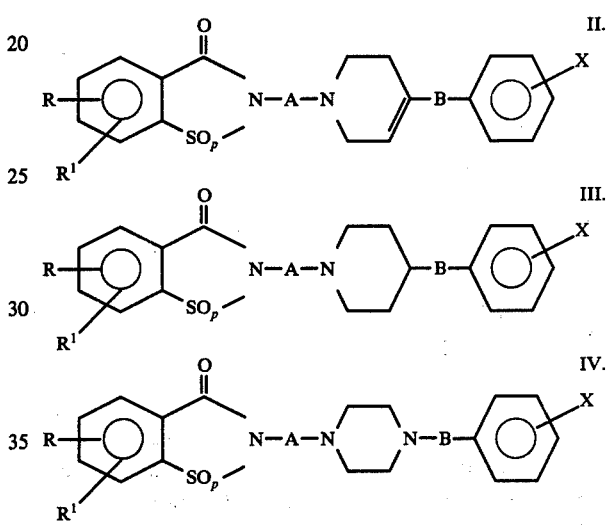

The preferred compounds of the invention are those of formulae II and III wherein R is in the 5- or 6-position and $R^1$ is hydrogen, or R and $R^1$ are hydrogen, A is $(CH_2)_2$, B is a single bond, X is hydrogen and p is 0 or 2, and those of formula IV wherein R is in the 5- or 6-position and $R^1$ is hydrogen or R and $R^1$ are hydrogen, A is $(CH_2)_2$, B is a single bond, X is hydrogen, and p is 2.

The term "lower alkyl" as used herein refers to alkyl groups having 1 to 4 carbons, with methyl or ethyl being preferred.

The term "lower alkoxy" as used herein refers to lower alkyl groups as defined above attached to an oxygen atom, with methoxy being preferred.

The term "halogen" as employed herein refers to chlorine, bromine, iodine or fluorine with chlorine and bromine being preferred.

The compounds of formulae II and III wherein p is 0, that is,

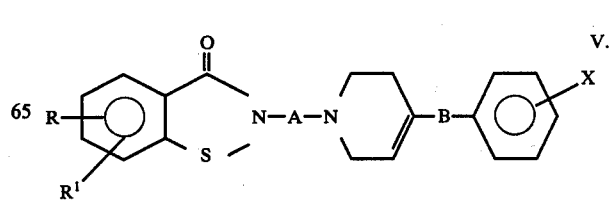

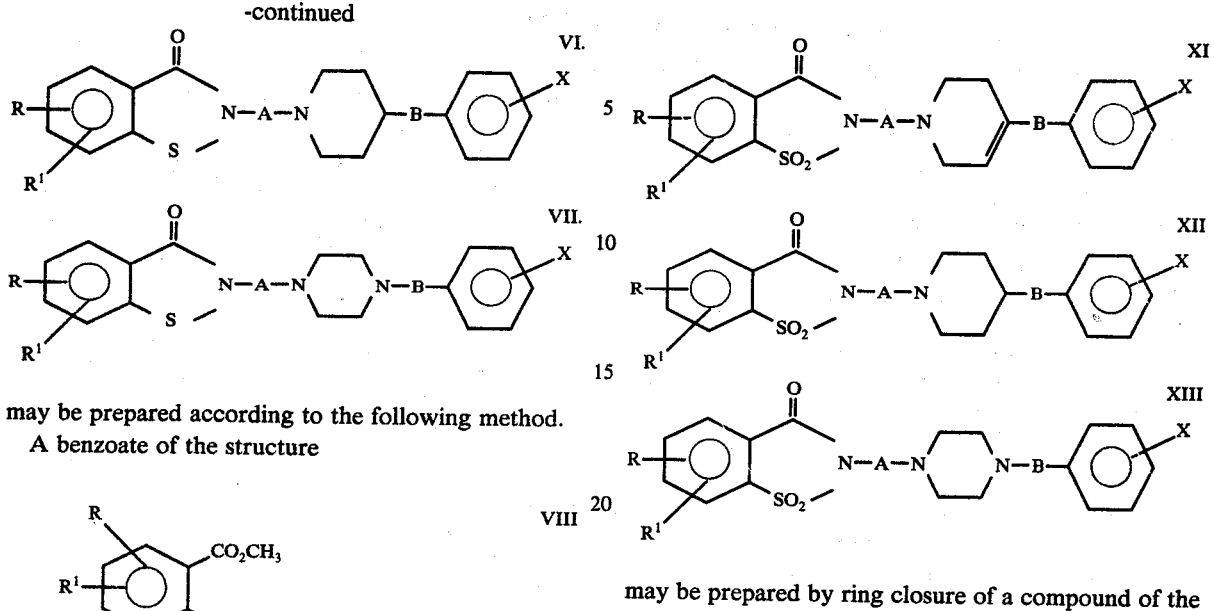

may be prepared according to the following method.

A benzoate of the structure

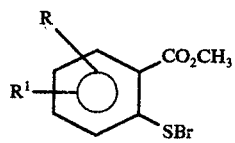

is reacted with an amine of the structure

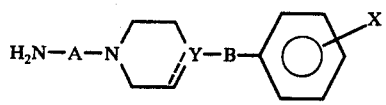

in the presence of an inert organic solvent, such as carbon tetrachloride, dioxane, dichloromethane or benzene, and preferably in the presence of an organic base, such as triethylamine, tri-n-butylamine, N-methylpiperidine or pyridine. The residue from the above reaction is refluxed in a lower alkanol, such as methanol or ethanol, containing an inorganic base, such as sodium hydroxide or potassium hydroxide, to give the compound of formulae V, VI or VII.

The starting material VIII in the above reaction is prepared by reaction of

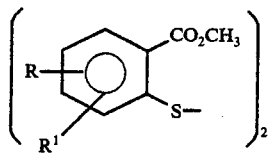

with bromine in the presence of an organic solvent, such as carbon tetrachloride (Grivas, J. Org. Chem., Vol. 40, No. 14 (1975), 2,029–2,032 and Chem. Abst. 27322t).

The starting materials IX and X employed in the above reaction are known in the art and may be prepared by conventional techniques. For example, with respect to X see Grivas, supra.

The compounds of formulae II, III AND IV wherein p is 2, that is

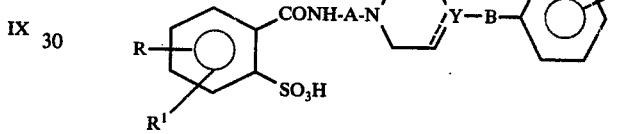

may be prepared by ring closure of a compound of the structure XIV

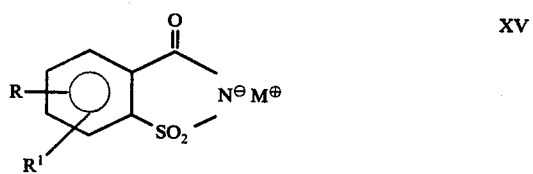

using a dehydrating agent, such as thionyl chloride and phosphorus pentachloride or phosphorus oxychloride.

Alternatively, compounds of the structures II, III and IV may be prepared by reacting a saccharin salt of the structure

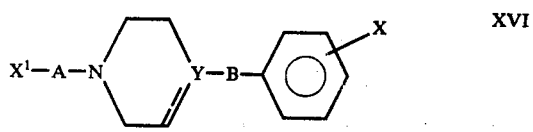

wherein M is a metal, such as $Na^+$, $K^+$, $Ca^{++}$ and the like with a compound of the structure wherein $X^1$ is a leaving group, such as Cl, Br, I or tosylate in a polar non-reacting solvent such as dimethylformamide at temperatures ranging from 50° to 200° C.

The starting materials XV and XVI are known in the art or may be prepared by standard techniques. Thus, the XVI starting material may be prepared by treating a compound of the structure

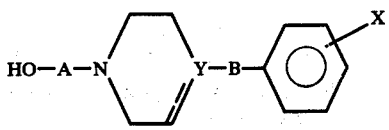

with a chlorinating agent, such as thionyl chloride, phosphorus oxychloride and the like.

Alternatively, the compounds of formulae XI, XII and XIII may be prepared by heating a compound of the structure

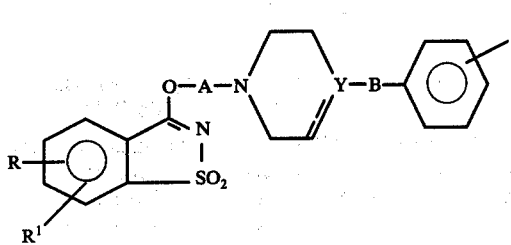

at a temperature within the range of from about 100° to about 250° C, preferably under vacuum.

The starting material of formula XIV in the above reaction may be prepared by refluxing of a sulfobenzoic anhydride of the structure XIX

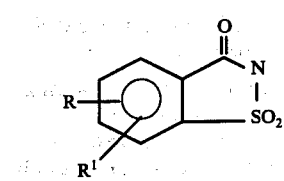

with an amine of formula IX in an aromatic solvent, such as benzene, toluene or xylene.

The starting material of formula XVIII may be prepared by reaction of a 3-substituted-1,2-benzisothiazole, 1,1-dioxide of the structure

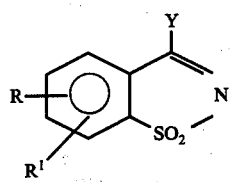

wherein Y is halogen, lower alkoxy, or mercapto with an alcohol of the structure

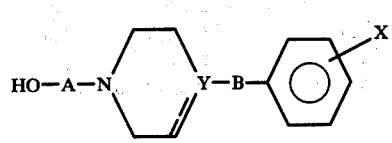

The formula XVII compound may be prepared by simple reaction of an amine of formula IX with ethylene oxide when A is (CH$_2$)$_2$ or with a compound of the structure

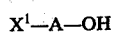     XX in a non-reacting solvent, such as benzene, dioxane, or DMF with the optional presence of a base, such as sodium carbonate or triethylamine.

Depending on the reaction conditions and the starting materials used, the new compounds are obtained in the free form or in the form of their acid-addition salts. The salts thereof can be converted into the free compounds in a known manner such as by reaction with a basic agent. Free bases which may be obtained can be converted into pharmaceutically acceptable acid-addition salts by reaction with a variety of acids. Acids useful for preparing these acid-addition salts include, inter alia, inorganic acids, such as the hydrohalic acids (e.g. hydrochloric and hydrobromic acids), sulfuric acid, nitric acid, and phosphoric acid, and organic acids, such as maleic, fumaric, tartaric, citric, acetic, benzoic, 2-acetoxybenzoic, salicyclic, succinic, nicotinic, methanesulfonic or cyclohexanesulfamic.

The compounds of formula I have antiflammatory activity as measured by the reverse passive arthus (RPA) (M. B. Goldlust and W. F. Schreiber, Agents and Actions, 5, 39 (1975)) or other related tests and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg to about 150 mg per kg of body weight per day.

The new compounds of the present invention including the acid-addition salts are also capable of modifying the central nervous system. When administered to mice, cats, rats, dogs, and other mammalian species in amounts ranging from about 1 mg to about 200 mg per kg of body weight per day, these compounds in particular exhibit central nervous system depressant activity, and can be used as tranquilizers for the relief of anxiety and tension states in the manner of chlordiazepoxide and as sedatives, for example, to promote sleep in anxious or tense subjects. These compounds also exhibit muscle relaxant activity. A preferred dosage regimen for optimum results would be from about 1 mg to about 10 mg per kg of body weight per day, and such dosage units are employed so that a total of from about 35 mg to about 6 g of active ingredient in single or divided doses are administered in a 24 hour period.

For any of these pharmaceutical purposes a compound or mixture of compounds of formula I or their pharmaceutically acceptable acid-addition salts may be administered orally or parenterally in a conventional dosage form, such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the Centigrade scale.

EXAMPLE 1

2-[2-(3,6-Dihydro-4-phenyl-1(2H)-pyridinyl)ethyl]-1,2-benzothiazol-3(2H)-one, hydrochloride (1:1)

2.90 g (18.2 mM) Bromine is dissolved in 25 ml of carbon tetrachloride and is added dropwise to 6.07 g (18.2 mM) dimethyl 2,2'-dithiodibenzoate and stirred as a suspension in 25 ml of carbon tetrachloride. After the addition is complete, the red solution is stirred for 30 minutes and added dropwise to a stirred solution of 10.0 g (36.4 mM) 3,6-dihydro-4-phenyl-1(2H)-pyridineethanamine, hydrochloride (1:2) and 5.07 ml (36.4 mM) of triethylamine in 50 ml of carbon tetrachloride. The mixture is stirred overnight, diluted with chloroform, washed with 5% KOH, water, dried ($Na_2SO_4$), and the solvents evaporated.

The residue is refluxed in 100 ml ethanol containing 150 mg sodium hydroxide for 4 hours. The ethanol is evaporated and the residue taken up in ether which is washed with water and evaporated to dryness.

The residue is chromatographed on silica gel (5 × 20 cm) eluted with chloroform (500 ml fractions). The first 4 fractions are combined, the chloroform evaporated and the residue dissolved in 200 ml ethanol. The salt is precipitated by adding 15 ml of 1 N HCl and 250 ml water. It is filtered out, washed with water, and dried at 80°/vacuum overnight to give 3.8 g of the title compound, m.p. 221°–223°.

EXAMPLE 2

2-[2-(3,6-Dihydro-4-phenyl-1(2H)-pyridinyl)ethyl]-1,2-benzothiazol-3(2H)-one, 1,1-dioxide

A.

2-[[[2-(4-Phenyl-1-(2H)-pyridinyl)ethyl]amino]-carbonyl]benzenesulfonic acid 8.80 g (43.6 mM) 3,6-Dihydro-4-phenyl-1(2H)pyridineethanamine, and 8.04 g (43.6 mM) o-sulfobenzoic anhydride are refluxed in 400 ml toluene for 1 hour, and stirred at room temperature overnight. The resulting precipitate is filtered out, washed with toluene, and dissolved in 1% NaOH. The solution is washed with chloroform. The product is precipitated from the aqueous layer by adding concentrated HCl slowly (if the basic solution is acidified all at once, the HCl salt precipitates): 10.12 g, m.p. 272°–274° (m.p. depends upon the rate of heating).

B.

2-[2-(3,6-Dihydro-4-phenyl-1(2H)-pyridinyl)-ethyl]-1,2-benzothiazol-3(2H)-one, 1,1-dioxide 7.17 g (18.6 mM) 2-[[[2-3,6-Dihydro-4-phenyl-1(2H)-pyridinyl)ethyl]amino]carbonyl]benzenesulfonic acid is dissolved in 35 ml of thionyl chloride containing 2.5 g of phosphorous pentachloride and refluxed for 1 hour. The thionyl chloride is evaporated in vacuo and the residue taken up in chloroform/water and neutralized with 50% sodium hydroxide. The chloroform layer is washed with saturated aqueous sodium chloride and evaporated in vacuo. The residue is recrystallized from alcohol to give 3.0 g of the title compound, m.p. 90°–92°.

EXAMPLE 3

2-[(4-Phenyl-1-piperazinyl)ethyl]-1,2-benzoisothiazol-3(2H)-one, 1,1-dioxide, hydrochloride (1:1)

A. 3-Chloro-1,2-benzisothiazole-1,1-dioxide (Pseudo saccharin chloride)

Reference: Japanese Patent No. 048934

100 g (545 mM) Saccharin, 100 ml thionyl chloride, 4 ml DMF (catalyst), and 400 ml dioxane are refluxed overnight. Thionyl chloride (50 ml) and DMF (1 ml) are added to the reaction mixture which is refluxed overnight again. The reaction mixture is evaporated and the residue recrystallized from toluene: 73.4 g, m.p. 140°–145° [lit. m.p. 148°–149°].

B.

3-[2-(4-Phenyl-1-piperazinyl)ethoxy]-1,2-benzisothiazole, 1,1-dioxide, hydrochloride (1:1)

13.2 g (65.5 mM) 3-Chloro-1,2-benzisothiazole, 1,1-dioxide dissolved in 150 ml acetone is added to 15.9 g (65.5 mM) 4-phenyl-1-piperazineethanol, hydrochloride (1:1) dissolved in 150 ml acetone, dropwise over 15 minutes. The mixture is refluxed for 30 minutes. After stirring for 1 hour at room temperature, the precipitate is filtered out and washed with acetone, and dried at 80°/vacuum to give 23.4 g of the title B compound. The compound softens at about 190° and melts at approximately 270° with decomposition.

C.

2-[(4-Phenyl-1-piperazinyl)ethyl]-1,2-benzoisothiazol-3(2H)-one, 1,1-dioxide, hydrochloride (1:1)

10.0 g (27.0 mM) 3-[2-(4-Phenyl-1-piperazinyl)-ethoxy]-1,2-benzisothiazole, 1,1-dioxide is heated at 135° under vacuum for 30 minutes. The fused material is dissolved in chloroform which is filtered from a small amount of insoluble material and evaporated. The residue is recrystallized from 250 ml alcohol to give the free base (2-[(4-phenyl-1-piperazinyl)ethyl]-1,2-benzoisothiazol-3(2H)-one, 1,1-dioxide), m.p. 115°–117°.

The free base is dissolved in dioxane and the salt precipitated with HCl/dioxane. The salt is filtered out, washed with dioxane and dried at 150°/vacuum to give 4.35 g of the title compound, m.p. 253°–255°.

EXAMPLE 4

2-[(4-Benzyl-1-piperazinyl)ethyl]-1,2-benzisothiazol-3(2H)-one, 1,1-dioxide

Ref. Giam et al, Org. Prep Proced. 6, 1 (1974)

To a stirred solution of 0.02 mol of sodium saccharin in 20 ml of DMF is added 0.02 mol of 2-(chloroethyl)-benzyl piperazine. The solution is heated under reflux for 30 minutes (white solid precipitates) and filtered hot. The filtrate is evaporated to dryness and the residue taken up in $CHCl_3$. The $CHCl_3$ layer is washed with water, dried ($Na_2SO_4$), and evaporated to dryness. The residue is recrystallized from ethanol to yield the title compound.

EXAMPLES 5 TO 19

Following the procedure of Example 1, but substituting for the dimethyl-2,2'-dithiobenzoate, the compound shown in Column I of Table A below, and substituting for the 3,6-dihydro-4-phenyl-1(2H)-pyridineethanamine, the compound shown in Column II, the compound of the invention shown in Column III is obtained.

TABLE A

| Ex. No. | Column I | R (position) | R¹ (position) | Column II | Column III |
|---|---|---|---|---|---|
| | (structure with CO₂CH₃, S—, R, R¹ on benzene ring)₂ | | | H₂N—A—N⟨piperidine⟩—Y—B—⟨phenyl-X⟩ | (structures with piperidine/tetrahydropyridine linked to benzothiophene carbonyl and to phenyl-X) As in Column I / As in Column II |
| 5. | | NO₂(5) | H | H₂N—(CH₂)₂—⟨piperidine⟩—⟨phenyl-OCH₃⟩ | |
| 6. | | NO₂(4) | H | H₂N—(CH₂)₃—⟨tetrahydropyridine⟩—⟨phenyl-CH₃(4)⟩ | |
| 7. | | Cl(5) | H | H₂N—(CH₂)₄—⟨tetrahydropyridine⟩—⟨phenyl-Cl⟩ | |
| 8. | | Cl(3) | H | H₂N—(CH₂)₂—HN—⟨tetrahydropyridine⟩—CH₂—⟨phenyl-CF₃(3)⟩ | |
| 9. | | Cl(5) | Cl(4) | H₂N—(CH₂)₂—N⟨piperazine⟩—(CH₂)₃—⟨phenyl⟩ | |
| 10. | | Br(4) | H | H₂N(CH₂)₂—N⟨piperazine⟩—(CH₂)₃—⟨phenyl-CH₃(3)⟩ | |

TABLE A-continued

| | Column I | Column II | Column III | | |
|---|---|---|---|---|---|
| | (bis-ester structure with CO$_2$CH$_3$ and S— on benzene ring, R/R$^1$ positions) | H$_2$N—A—N⟨piperidine⟩—Y—B—⟨phenyl-X⟩ | (benzothiazinone-type structure) —N—A—N⟨piperidine⟩—Y—B—⟨phenyl-X⟩ | (piperidine) —A—N⟨piperidine⟩—Y—B—⟨phenyl-X⟩ | |
| Ex. No. | R (position) | R$^1$ (position) | Column II structure | R (position) | R$^1$ (position) |
| | | | | As in Column I | As in Column II |

| Ex. No. | R (position) | R$^1$ (position) | Column II |
|---|---|---|---|
| 11. | F(5) | H | H$_2$N(CH$_2$)$_4$—N⟨piperazine⟩—(CH$_2$)$_3$—⟨phenyl-CF$_3$⟩ |
| 12. | CH$_3$(4) | H | H$_2$N—(CH$_2$)$_3$—N⟨piperazine⟩—⟨phenyl⟩ |
| 13. | i-propyl(3) | H | H$_2$N(CH$_2$)$_2$—N⟨piperidine⟩—CH$_2$—⟨phenyl⟩ |
| 14. | CH$_3$O(5) | H | H$_2$N—(CH$_2$)$_5$—N⟨piperidine⟩—(CH$_2$)$_2$—⟨phenyl-CH$_3$⟩ |
| 15. | Cl(5) | Cl(4) | H$_2$N—(CH$_2$)$_4$—N⟨piperidine⟩—⟨phenyl⟩ |
| 16. | CH$_3$O(5) | CH$_3$O(3) | H$_2$N—(CH$_2$)$_2$—N⟨piperidine⟩—(CH$_2$)$_2$—⟨phenyl⟩ |
| 17. | NO$_2$(3) | H | H$_2$N—(CH$_2$)$_3$—N⟨piperazine⟩—(CH$_2$)$_2$—⟨phenyl-CH$_3$⟩ |

TABLE A-continued

| Ex. No. | Column I R (position) | R¹ (position) | Column II | Column III R (position) | R¹ (position) |
|---|---|---|---|---|---|
| 18. | CH₃(6) | H | H₂N—(CH₂)₅—N(piperazine)—CH₂—phenyl | As in Column I | As in Column II |
| 19. | CH₃(4) | H | H₂N—(CH₂)₂—N(tetrahydropyridine)—(CH₂)₂—phenyl | As in Column I | As in Column II |

EXAMPLES 20 TO 34

Following the procedure of Example 2, but substituting for the 3,6-dihydro-4-phenyl-1(2H)-pyridineethanamine, the compound shown in Column I of Table B below, and substituting for o-sulfobenzoic anhydride, the compound shown in Column II, the compound of the invention shown in Column III is obtained.

TABLE B

| Ex. No. | Column I<br>(structure with H₂N—A—Y—⟨phenyl-X⟩—B) | Column II<br>(benzisothiazole-type with R, R¹) | | Column III<br>(As in Column I / As in Column II) |
|---|---|---|---|---|
| | | R (position) | R¹ (position) | |
| 20. | H₂N—(CH₂)₂—N⟨piperidine⟩—CH₂—⟨phenyl-OCH₃⟩ | NO₂(5) | H | As in Column I / As in Column II |
| 21. | H₂N—(CH₂)₃—N⟨piperidine⟩—(CH₂)₂—⟨phenyl-CH₃⟩ | NO₂(4) | H | |
| 22. | H₂N—(CH₂)₃—N⟨piperidine⟩—⟨phenyl-Cl⟩ | Cl(5) | H | |
| 23. | H₂N—(CH₂)₂—N⟨piperidine⟩—⟨phenyl-CF₃⟩ | Cl(7) | H | |
| 24. | H₂N—(CH₂)₃—N⟨piperazine⟩—N—⟨phenyl⟩ | Cl(5) | Cl(6) | |
| 25. | H₂N—(CH₂)₂—N⟨piperazine⟩—N—CH₂—⟨phenyl⟩ | Br(6) | H | |

TABLE B-continued

| Ex. No. | Column I | R (position) | R¹ (position) | Column II | Column III |
|---|---|---|---|---|---|
| 26. | H₂N—(CH₂)₂—N(piperazine)N—B—phenyl-X | F(5) | H | As in Column II | As in Column I |
| 27. | H₂N—(CH₂)₃—N(piperazine)N—B—(3-CF₃-phenyl)-X | CH₃(6) | H | As in Column II | As in Column I |
| 28. | H₂N—(CH₂)₅—N(piperidine)—CH₂—phenyl-X | i-propyl(6) | H | As in Column II | As in Column I |
| 29. | H₂N—(CH₂)₄—N(piperidine)—(4-CH₃-phenyl)-X | CH₃O(5) | H | As in Column II | As in Column I |
| 30. | H₂N—(CH₂)₄—N(piperidine)—(4-Cl-phenyl)-X | Cl(5) | Cl(6) | As in Column II | As in Column I |
| 31. | H₂N—(CH₂)₃—N(piperidine)—(CH₂)₂—(4-Br-phenyl)-X | CH₃O(5) | CH₃O(6) | As in Column II | As in Column I |
| 32. | H₂N—(CH₂)₂—N(piperazine)N—CH₂—(4-C₂H₅-phenyl)-X | NO₂(7) | H | As in Column II | As in Column I |

TABLE B-continued
| Ex. No. | Column I | Column II | | | Column III | |
|---|---|---|---|---|---|---|
| | | R (position) | R¹ (position) | | R (position) | R¹ (position) |
| 33. | 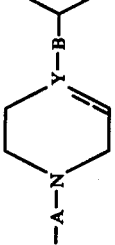 | $CH_3(6)$ | H | | As in Column II | As in Column I |
| 34. | 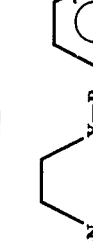 | $CH_3(7)$ | H | | | |

EXAMPLES 35 to 49

Following the procedure of Example 3, but substituting for 3-chloro-1,2-benzisothiazole, 1,1-dioxide, the compound shown in Column II of Table C below, and substituting for 4-phenyl-1-piperazineethanol, hydrochloride, the compound shown in Column I, the compound of the invention shown in Column III is obtained.

TABLE C

| | Column I | | Column II | | | Column III | |
|---|---|---|---|---|---|---|---|
| Ex. No. | HO—A—N⟨⟩—Y—B—⟨⟩—X | R (position) | R¹ (position) | y | R (position) | R¹ (position) | As in Column I / As in Column II |
| 35. | HO—(CH$_2$)$_2$—N⟨⟩=⟨⟩—(CH$_2$)$_2$—⟨⟩—OCH$_3$ | NO$_2$(5) | H | Cl | | | |
| 36. | HO—(CH$_2$)$_3$—N⟨⟩=⟨⟩—⟨⟩—CH$_3$ | NO$_2$(4) | H | Br | | | |
| 37. | HO—(CH$_2$)$_4$—N⟨⟩=⟨⟩—⟨⟩—Cl | Cl(5) | H | Cl | | | |
| 38. | HO—(CH$_2$)$_5$—N⟨⟩=⟨⟩—CH$_2$—⟨⟩—CF$_3$ | Cl(7) | H | Cl | | | |
| 39. | HO—(CH$_2$)$_2$—N⟨⟩N—(CH$_2$)$_3$—⟨⟩ | Cl(5) | Cl(6) | Cl | | | |
| 40. | HO—(CH$_2$)$_3$—N⟨⟩N—(CH$_2$)$_3$—⟨⟩ | Br(6) | H | CH$_3$ | | | |

TABLE C-continued

| Ex. No. | Column I | Column II R (position) | R¹ (position) | y | Column III R (position) | R¹ (position) |
|---|---|---|---|---|---|---|
| 41. | HO—(CH₂)₂—N(piperazine)N—(CH₂)₃—phenyl | F(5) | H | SH | As in Column II | As in Column I |
| 42. | HO—(CH₂)₃—N(piperazine)N—3-CF₃-phenyl | CH₃(6) | H | CH₃O | | |
| 43. | HO—(CH₂)₂—N(piperidine, 4-CH₂-phenyl) | i-propyl (6) | H | CH₃O | | |
| 44. | HO—(CH₂)₂—N(piperidine, 4-(CH₂)₂-(4-CH₃-phenyl)) | CH₃O(5) | H | Cl | | |
| 45. | HO—(CH₂)₃—N(piperidine, 4-phenyl) | Cl(5) | Cl(6) | Cl | | |
| 46. | HO—(CH₂)₂—N(piperidine, 4-(CH₂)₂-phenyl) | CH₃O(5) | CH₃O(6) | Cl | | |
| 47. | HO—(CH₂)₂—N(piperazine)N—(CH₂)₂—phenyl | NO₂(7) | H | Br | | |

TABLE C-continued

| Ex. No. | Column I | Column II | | | Column III |
|---|---|---|---|---|---|
| | | R (position) | R¹ (position) | y | |
| 48. | HO—(CH$_2$)$_3$—N[piperidine]N—CH$_2$—[phenyl-X] | CH$_3$(6) | H | Cl | As in Column I / As in Column II |
| 49. | HO—(CH$_2$)$_5$—N[piperidine]—(CH$_2$)$_2$—[phenyl-X] | CH$_3$(7) | H | Cl | As in Column I / As in Column II |

EXAMPLES 50 TO 64

Following the procedure of Example 4, but substituting for the 2-(chloroethyl)benzylpiperazine, the compound shown in Column I of Table D below, and substituting for sodium saccharin, the compound shown in Column II, the compound of the invention shown in Column III is obtained.

TABLE D

| | Column I | Column II | | | Column III |
|---|---|---|---|---|---|
| Ex. No. | (structure with X¹–A–N, Y–B–phenyl-X) | R (position) | R¹ (position) | M⊕ | As in Column I / As in Column II |
| 50. | Cl—(CH₂)₂—N (4-piperidinyl)-CH₂-phenyl-OCH₃ | NO₂(5) | H | Na | |
| 51. | Br—(CH₂)₅—N (4-piperidinyl)-(CH₂)₂-phenyl-CH₃ | NO₂(4) | H | K | |
| 52. | Cl—(CH₂)₅—N (4-piperidinyl)-phenyl-Cl | Cl(5) | H | Na | |
| 53. | Br—(CH₂)₂—N (4-piperidinyl)-phenyl-CF₃ | Cl(7) | H | K | |
| 54. | Cl—(CH₂)₃—N (piperazinyl)-(CH₂)₃-phenyl | Cl(5) | Cl(6) | Na | |
| 55. | Cl—(CH₂)₂—N (piperazinyl)-CH₂-phenyl | Br(6) | H | K | |

TABLE D-continued

| Ex. No. | Column I | Column II R (position) | R¹ (position) | M⊕ | Column III |
|---|---|---|---|---|---|
| | X¹—A—N⟨⟩Y—B—⟨phenyl⟩—X | ⟨benzisothiazolone structure⟩ R, R¹ | | | ⟨product structure⟩ |
| 56. | Br—(CH₂)₂—N⟨piperidine⟩N—(CH₂)₂—⟨phenyl⟩ | F(5) | H | Ca | As in Column I / As in Column II |
| 57. | Cl—(CH₂)₃—N⟨piperidine⟩N—(CH₂)₃—⟨phenyl-CF₃⟩ | CH₃(6) | H | Na | |
| 58. | Br—(CH₂)₃—N⟨piperidine⟩—CH₂—⟨phenyl⟩ | i-propyl (6) | H | K | |
| 59. | Br—(CH₂)₄—N⟨piperidine⟩—⟨phenyl-CH₃⟩ | CH₃O(5) | H | K | |
| 60. | Br—(CH₂)₄—N⟨piperidine⟩—⟨phenyl-Cl⟩ | Cl(5) | Cl(6) | Na | |
| 61. | Cl—(CH₂)₃—N⟨tetrahydropyridine⟩—(CH₂)₂—⟨phenyl-Br⟩ | CH₃O(5) | CH₃O(6) | Na | |
| 62. | tosyl—CH₂—N⟨piperazine⟩N—CH₂—⟨phenyl-C₂H₅⟩ | NO₂(7) | H | Na | |

TABLE D-continued

| | Column I | Column II | | | Column III | | |
|---|---|---|---|---|---|---|---|
| Ex. No. | X¹—A—N⟨⟩=⟨⟩—Y—B—⟨⟩—X | ⟨R,R¹-phenyl⟩—C(O)—CH(N⊖ M⊕)—SO₂ (fused) | R (position) | R¹ (position) | ⟨R,R¹-phenyl⟩—C(O)—CH(NH)—SO₂ —A—N⟨⟩=⟨⟩—Y—B—⟨⟩—X | R (position) | R¹ (position) |
| 63. | tosyl—(CH₂)₃—N⟨piperazine⟩N—CH₂—phenyl | | CH₃(6) | H | | As in Column II | As in Column I |
| 64. | tosyl—(CH₂)₅—N⟨piperidinyl⟩—phenyl | | CH₃(7) | H | | | |

What is claimed is:
1. A compound of the structure

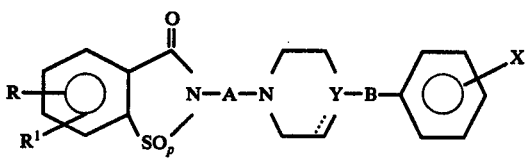

wherein R is hydrogen, halogen, lower alkyl, lower alkoxy, or nitro; R¹ is hydrogen, lower alkoxy or halogen, with the proviso that R¹ can be lower alkoxy or halogen only when R is lower alkoxy or halogen, respectively; X is hydrogen, halogen, lower alkyl, lower alkoxy, or trifluoromethyl; Y is C or N, where Y is C, ----- represents a double bond, and when Y is N,----- represents a single bond, A is an alkylene group containing 2 to 5 carbons; and B is a single bond or an alkylene group containing from 1 to 3 carbons, and physiologically acceptable acid-addition salts thereof.

2. The compound of claim 1 having the structure

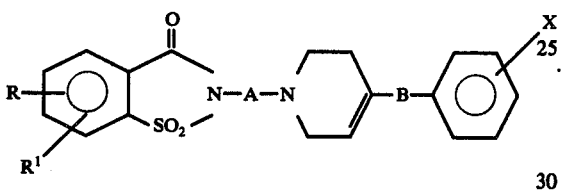

3. The compound of claim 1 having the structure

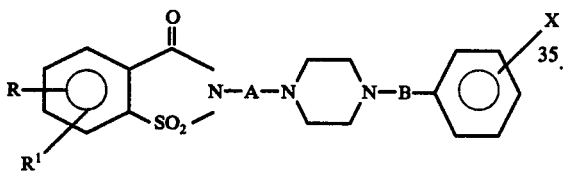

4. The compound of claim 1 wherein R and R¹ are hydrogen.

5. The compound of claim 1 wherein R is in the 5- or 6-position and R¹ is hydrogen.

6. The compound of claim 2 wherein R is hydrogen, A is (CH₂)₂, B is a single bond, X is hydrogen.

7. The compound of claim 3 wherein R is hydrogen, A is (CH₂)₂, B is a single bond, X is hydrogen.

8. The compound of claim 1 wherein A is —(CH₂)₂— or —(CH₂)₃—.

9. A compound as defined in claim 1 having the name 2-[2-(3,6-dihydro-4-phenyl-1(2H)-pyridinyl)ethyl]-1,2-benzisothiazol-3(2H)-one, 1,1-dioxide.

10. A compound as defined in claim 1 having the name 2-[(4-phenyl-1-piperazinyl)ethyl]-1,2-benzisothiazol-3(2H)-one, 1,1-dioxide, or its hydrochloride salt.

11. A compound of the structure

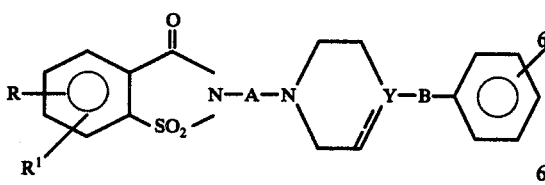

wherein R is hydrogen, halogen, lower alkyl, lower alkoxy, or nitro; R¹ is hydrogen, lower alkoxy or halogen, with the proviso that R¹ can be lower alkoxy or halogen only when R is lower alkoxy or halogen, respectively; X is hydrogen, halogen, lower alkyl, lower alkoxy, or trifluoromethyl; Y is C or N, where Y is C, ----- represents a single or double bond, and when Y is N,----- represents a single bond, A is an alkylene group containing 2 to 5 carbons; and B is a single bond or an alkylene group containing from 1 to 3 carbons, and physiologically acceptable acid-addition salts thereof.

12. A compound as defined in claim 11 having the name 2-[2-(3,6-dihydro-4-phenyl-1(2H)-pyridinyl)ethyl]-1,2-benzisothiazol-3(2H)-one or its hydrochloride salt.

13. The compound of claim 11 having the structure

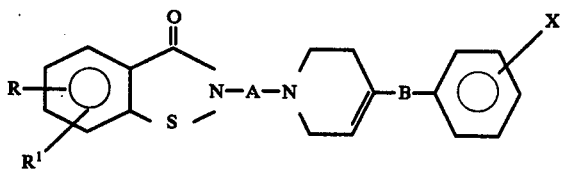

14. The compound of claim 13 wherein R is hydrogen, A is (CH₂)₂, B is a single bond, X is hydrogen.

15. The compound of claim 11 having the structure

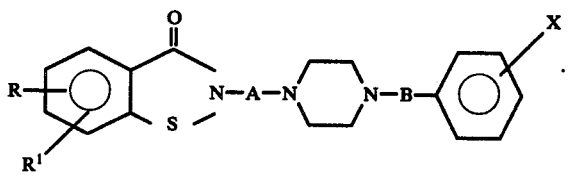

16. The compound of claim 11 having the structure

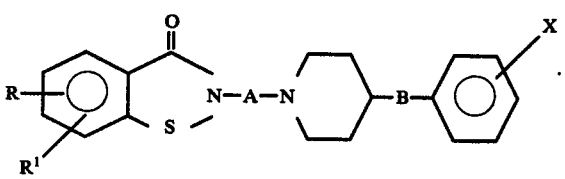

17. The compound of claim 11 wherein R and R¹ are hydrogen.

18. A composition which comprises a compound of claim 1 in a physiologically acceptable vehicle, said compound being present in an effective amount for treating an inflammatory condition.

19. A method for treating an inflammatory condition in a mammalian host, which comprises administering an effective amount of the composition of claim 18.

20. A method for treating anxiety in a mammalian host, which comprises administering an effective amount of the composition of claim 18.

21. A composition which comprises a compound of claim 11 in a physiologically acceptable vehicle, said compound being present in an effective amount for treating an inflammatory condition.

22. A method for treating an inflammatory condition in a mammalian host, which comprises administering an effective amount of the composition of claim 21.

23. A method for treating anxiety in a mammalian host, which comprises administering an effective amount of the composition of claim 21.

* * * * *

UNITED STATES PATENT AND TRADEMARK OFFICE
CERTIFICATE OF CORRECTION

PATENT NO. : 4,110,449
DATED : August 29, 1978
INVENTOR(S) : Peter C. Wade

It is certified that error appears in the above-identified patent and that said Letters Patent are hereby corrected as shown below:

Table C, Ex. 35-49, Column II, column heading "y" should read --Y--.
Table D, Ex. 63, the structure in Column I should read -- tosyl-$(CH_2)_3$-N  --.

Col. 39, Claim 1, in the structure, "$SO_p$" should read --$SO_2$--.
Col. 39, Claim 11, in the structure, "$SO_2$" should read --S--.

Signed and Sealed this

Eighth Day of May 1979

[SEAL]

Attest:

RUTH C. MASON
Attesting Officer

DONALD W. BANNER
Commissioner of Patents and Trademarks